(12) United States Patent
Cerri et al.

(10) Patent No.: US 9,127,037 B2
(45) Date of Patent: Sep. 8, 2015

(54) CRYSTALLINE ROSTAFUROXIN

(75) Inventors: Alberto Cerri, Milan (IT); Silvia Armaroli, Gallo Poggio Renatico (IT); Marco Torri, Rho (IT)

(73) Assignee: ROSTAQUO S.P.A., Pomezia (RM) (IT)

( * ) Notice: Subject to any disclaimer, the term of this patent is extended or adjusted under 35 U.S.C. 154(b) by 1529 days.

(21) Appl. No.: 12/094,885

(22) PCT Filed: Nov. 23, 2006

(86) PCT No.: PCT/EP2006/068845
§ 371 (c)(1),
(2), (4) Date: Aug. 4, 2008

(87) PCT Pub. No.: WO2007/060206
PCT Pub. Date: May 31, 2007

(65) Prior Publication Data
US 2008/0300228 A1    Dec. 4, 2008

(30) Foreign Application Priority Data
Nov. 25, 2005    (EP) .................................... 05025817

(51) Int. Cl.
*C07J 17/00*    (2006.01)

(52) U.S. Cl.
CPC ...................... *C07J 17/00* (2013.01)

(58) Field of Classification Search
CPC ............. A61K 31/58; A61P 9/00; C07J 17/00
USPC .......................................... 514/172; 552/612
See application file for complete search history.

(56) References Cited

U.S. PATENT DOCUMENTS

| | | | | |
|---|---|---|---|---|
| 5,432,169 A | * | 7/1995 | Quadri et al. ................. | 514/172 |
| 5,567,697 A | * | 10/1996 | Quadri et al. ................. | 514/176 |
| 5,591,734 A | * | 1/1997 | Quadri et al. ................. | 514/172 |
| 5,593,982 A | * | 1/1997 | Quadri et al. ................. | 514/172 |
| 5,731,345 A | * | 3/1998 | Gobbini et al. ............... | 514/461 |

FOREIGN PATENT DOCUMENTS

EP    0 583 578 A    2/1994

OTHER PUBLICATIONS

Quadri L et al "17[beta]-(3-Furyl)-5[beta]-androstane-3[beta]-14[beta],17[alpha]-triol (PST 2238). A very potent antihypertensive agent with a novel mechanism of action" Journal of Medicinal Chemistry 1997 United States, vol. 40, No. 11, 1997, pp. 1561-1564.
Supporting Information for J.Med. Chem. vol. 40 (11) pp. 1561-1564 (Experimental Section) 1997, pp. 1-5.

* cited by examiner

*Primary Examiner* — Sabiha N Qazi
(74) *Attorney, Agent, or Firm* — Lucas & Mercanti, LLP (57) ABSTRACT

New crystalline forms of 17β-(3-Furyl)-5-βandrostane-3β, 14β,17α-triol are described together with pharmaceutical composition containing the same and methods for their preparation. In particular new Forms B, C, D, E and H are here described.

7 Claims, 9 Drawing Sheets

Figure 1: Rostafuroxin Form A, X-ray diffractogram.

Figure 2: Rostafuroxin Form B, X-ray diffractogram.

Figure 3: Rostafuroxin Form C, X-ray diffractogram.

Figure 4: Rostafuroxin Form D, X-ray diffractogram.

Figure 5: Rostafuroxin Form E, X-ray diffractogram.

Figure 6: Rostafuroxin Form F, X-ray diffractogram

Figure 7: Rostafuroxin Form G, X-ray diffractogram

Figure 8: Rostafuroxin Form H, X-ray diffractogram

Figure 9: Amorphous Rostafuroxin, X-ray diffractogram

CRYSTALLINE ROSTAFUROXIN

FIELD OF THE INVENTION

The present invention relates to new crystalline forms of 17β-(3-furyl)-5β-androstane-3β,14β,17α-triol, pharmaceutical composition containing the same and methods for their preparation.

BACKGROUND OF THE INVENTION

The synthesis and the biological activity of 17β-(3-furyl)-5β-androstane-3β,14β,17α-triol (INN: rostafuroxin, also named PST2238) has been described in U.S. Pat. No. 5,591,734. This patent discloses a class of 17-(3-furyl) and (4-pyridazinyl)-5β,14β-androstane derivatives, active on the cardiovascular system and useful in the pharmaceutical field for the treatment of cardiovascular disorders such as heart failure and hypertension.

It has been shown (see Ferrari P. et al., J Pharmacol Exp Ther. 1998 April; 285(1):83-94) that this compound acts as selective inhibitor of the ouabain pressor effect. In vitro, rostafuroxin displaced ouabain from its binding sites on purified sodium, potassium ATPase enzyme (Na—K ATPase) ($IC_{50}$ $1.7 \times 10^{-6}$ M) without interacting with other receptors involved in blood pressure regulation or hormonal control. In cultured renal cells, incubation with ouabain ($10^{-10}$ to $10^{-8}$ M) for 5 days stimulated the Na—K pump at Vmax, whereas rostafuroxin showed the same effect at micromolar concentration. The ouabain-dependent increase in the Na—K pump rate was abolished by rostafuroxin at concentrations from $10^{-14}$ to $10^{-9}$ M. In rats made hypertensive by chronic infusion of 50 microg/kg/day of ouabain, rostafuroxin given per os at very low doses (0.1-1 microg/kg/day for 4 weeks) abolished the increase in blood pressure and renal Na—K ATPase activity caused by ouabain. Rostafuroxin did not affect either blood pressure or renal Na—K ATPase activity in normotensive rats. In conclusion, rostafuroxin has been shown to be a very potent compound that normalizes blood pressure and alterations in the Na—K pump caused by ouabain. Thus it represents the prototype of a new class of antihypertensive drugs that could be effective in forms of hypertension sustained by the concomitant increase of endogenous ouabain levels and alterations in the Na—K pump.

Primary hypertension is a clinical condition affecting 25-30% of the adult population in industrialized societies and through its cardiac, cerebral and renal complications is responsible for a large proportion of health burdens and costs. The anti-hypertensive drugs available are able to reduce the incidence of organ complications. However, this success is also limited because the present therapeutic approach ignores the enormous heterogeneity of hypertension in terms of environmental influences, genetic factors, organ complications and response to therapy.

A number of recent reviews have addressed the issue of the pharmacogenomics of primary hypertension and related complications by considering the data on the genotype-drug response relationship.

The applicant has long been involved in the search of molecular targets with a causal role for hypertension and its complications. The outcome was the detection of two molecular targets for hypertension and organ complications which are reciprocally related: a) mutations in the genes encoding the different of the cytoskeletal protein, adducin and b) increased circulating levels of endogenous ouabain (EO). The genetic association between adducin polymorphism and hypertension has been documented both in rats and humans.

A drug able to interfere with the cellular and molecular alterations caused by the mutated adducin and/or increased EO, namely upregulation of the renal Na—K pump may thus represent the appropriate hypertensive therapy for patients in which these mechanisms are at work. Rostafuroxin is the prototype of such a drug (Bianchi G. et al., Pharmacogenomics. 2003 May; 4(3):279-96).

Many drugs, old and new, were discovered and rushed into market as their 'suitable' crystalline forms and had never been screened thoroughly for their potential polymorphic forms. With the recent technological advancement of solid state chemistry, it is possible that new polymorphic forms can be discovered, which have never been seen before. The new polymorphic forms are often able to deliver therapeutic advantages and represent one of the new challenges of the pharmaceutical industry. As a matter of fact polymorphism, the ability of a molecule to crystallize into more than one crystal arrangement, can have a profound effect on the shelf life, solubility, formulation properties, and processing properties of a drug.

More seriously, the action of a drug can be affected by the polymorphism of the drug molecules. Different polymorphs can have different rates of uptake in the body, leading to lower or higher biological activity than desired. In extreme cases, an undesired polymorph can even be toxic. The occurrence of an unknown polymorphic form during manufacture can have an enormous impact on a drug company.

Therefore it is vital that researchers involved in the formulation of crystalline products be able to select the polymorph with the correct properties and anticipate problems such as the unwanted crystallization of other polymorphs.

Surprisingly, a very large number of pharmaceuticals exhibit the phenomenon of polymorphism. 70% of barbiturates, 60% of sulfonamides and 23% of steroids exist in different polymorphic forms.

Conducting a crystallization study on rostafuroxin led to the following observations, which then brought to the claimed invention.

DESCRIPTION OF THE INVENTION

First it has been discovered that rostafuroxin obtained following the procedure described in Example 1 of the U.S. Pat. No. 5,591,734 is amorphous, whereas the products obtained following the procedures described in J. Med. Chem., 1997; 40(11); 1561-1564 and its supporting information (see in particular page 2, lines 14-18) provide different crystalline forms (here after identified, characterized and named crystalline Form A, Form F and Form G).

It has also been discovered that further crystalline forms of rostafuroxin exist which show some advantages with respect to the amorphous form.

The present invention provides a method for preparing crystalline Form F of rostafuroxin, comprising dissolving any form of rostafuroxin (amorphous or any other crystalline form) in ethanol and then adding dropwise this solution to water at room temperature, followed by isolation of the crystalline rostafuroxin Form F, which thus precipitates. Preferably the isolation is carried out by filtration and after the isolation the resulting product is washed with water and dried under vacuum.

With respect to the other methods for obtaining the other crystalline forms this method to obtain Form F of rostafuroxin offers the advantage that only ethanol and water are employed in the crystallization, thus reducing the costs and the environmental impact, and the final product contains only water without traces of organic solvents. With respect to other methods for obtaining Form F this method provides the advantage of being easily scalable. Moreover adding dropwise the ethanol solution to water at room temperature avoids the use of high temperatures which may decompose the product to give the corresponding dehydrated derivative.

Another object of the present invention is a crystalline form of rostafuroxin which is selected from the group consisting of: Form B, Form C, Form D, Form E and Form H.

The invention further provides a method for preparing Form B of rostafuroxin, comprising suspending and heating any form of rostafuroxin (amorphous or any other crystalline form) in p-xylene, followed by isolation of the crystalline rostafuroxin Form B.

The invention further provides a method for preparing Form C of rostafuroxin, comprising dissolving any form of rostafuroxin (amorphous or any other crystalline form) in diethyl ether or toluene, followed by isolation of the crystalline rostafuroxin Form C.

The invention further provides a method for preparing Form D of rostafuroxin, comprising dissolving any form of rostafuroxin (amorphous or any other crystalline form) in ethyl acetate or ethyl acetate/diisopropyl ether, followed by isolation of the crystalline rostafuroxin Form D.

The invention further provides a method for preparing Form E of rostafuroxin comprising dissolving any form of rostafuroxin (amorphous or any other crystalline form) in isopropanol or isopropanol/diisopropyl ether, followed by isolation of the crystalline rostafuroxin Form E.

The invention further provides a method for making Form H of rostafuroxin, comprising dissolving any form of rostafuroxin (amorphous or any other crystalline form) in m-xylene, followed by isolation of the crystalline rostafuroxin Form H.

The crystalline Form C of rostafuroxin offers the advantage that it doesn't contain any amount of water nor any amount of other solvents employed during the preparation.

The method described to obtain crystalline Form D of rostafuroxin provides crystallization with high yield and offers the advantage that low amounts of organic solvents are employed.

The method described to obtain crystalline Form E of rostafuroxin offers the advantage that low amounts of organic solvents are employed. The crystallization provides a product having large particle size, that can be easily filtered and recovered with high yield.

The method described to obtain Form H of rostafuroxin provides the recovery of the product with high yield.

The crystalline Form B shows on X-ray diffraction a peak at an angle of refraction 2 theta ($\theta$), of 17.7±0.2 degrees; preferably it includes five more peaks at angles of refraction 2 theta ($\theta$) selected from the group consisting of 13.56, 15.55, 15.91, 14.37 and 8.92±0.02 degrees.

The crystalline Form C shows on X-ray diffraction a peak at an angle of refraction 2 theta ($\theta$), of 16.5±0.2 degrees; preferably it includes five more peaks at angles of refraction 2 theta ($\theta$) selected from the group consisting of 8.33, 14.49, 14.96, 10.84, 13.95±0.02 degrees.

The crystalline Form D shows on X-ray diffraction a peak at an angle of refraction 2 theta ($\theta$), of 17.1±0.2 degrees; preferably it includes five more peaks at angles of refraction 2 theta ($\theta$) selected from the group consisting of 15.23, 16.92, 13.32, 14.27, 23.14±0.02 degrees.

The crystalline Form E shows on X-ray diffraction a peak at an angle of refraction 2 theta ($\theta$), of 13.3±0.2 degrees; preferably it includes five more peaks at angles of refraction 2 theta ($\theta$) selected from the group consisting of 20.57, 14.07, 6.98, 3.60, 16.43±0.02 degrees.

The crystalline Form H shows on X-ray diffraction a peak at an angle of refraction 2 theta ($\theta$), of 13.5±0.2 degrees; preferably it includes five more peaks at angles of refraction 2 theta ($\theta$) selected from the group consisting of 15.97, 15.54, 16.34, 14.34, 16.96±0.02 degrees.

Another object of the present invention is a pharmaceutical composition comprising a crystalline form of rostafuroxin which is selected from the group consisting of: Form B, Form C, Form D, Form E and Form H, together with a pharmaceutically acceptable carrier or diluent or excipients.

A further object of the present invention is the use of a crystalline form of rostafuroxin which is selected from the group consisting of: Form B, Form C, Form D, Form E and Form H for the preparation of a pharmacological agent for the treatment of a cardiovascular disease; preferably for the treatment of heart failure or hypertension.

EXAMPLES

The powder X-ray diffraction were obtained by methods known in the art using a Philips PW1800 diffractometer.

The system used a copper X-ray source maintained at 50 kV and 30 mA to provide CuK$\alpha$ emission of 1.54056 Angstrom and a solid-state peltier cooled detector. Data were collected from 2° to 40° two-theta using a step scan of 0.02°/point with a one second/point counting time.

Comparative Example 1

Preparation of Rostafuroxin Form A

A mixture of 5.00 g of rostafuroxin (amorphous or any other crystalline form) and 30 ml of methanol was refluxed until the solution was clear, cooled to room temperature and stirred for 40 hours. The precipitate obtained was filtered and dried under vacuum at 40° C. for 16 hours. The product contained 50% molar (0.5 molar amount) methanol. Yield: 33%.

Comparative Example 2

Preparation of Rostafuroxin Form A

A mixture of 5.50 g of rostafuroxin (amorphous or any other crystalline form) and 33 ml of methanol was refluxed until clear solution; then 11 ml of diisopropyl ether were added to the warm solution. After cooling, the solution was left to room temperature for 96 hours. The precipitate obtained was filtered, washed with diisopropyl ether and dried at room temperature under vacuum for 16 hours. The product contained 50% molar (0.5 molar amount) methanol. Yield: 44%

Comparative Example 3

Preparation of Rostafuroxin Form A

A mixture of 5.00 g of rostafuroxin (amorphous or any other crystalline form) and 30 ml of methanol was refluxed until the solution was clear. 1 ml of water and 10 ml of methanol were added at reflux temperature. The clear solution was cooled to room temperature and stirred for 72 hours. The precipitate obtained was filtered and dried under vacuum at 40° C. for 24 hours. The product contained 50% molar (0.5 molar amount) methanol. Yield: 60%

Example 1

Preparation of Rostafuroxin Form B 5.00 g of rostafuroxin (amorphous or any other crystalline form) were suspended in 150 ml of p-xylene and warmed to 110° C. The solution was cooled at room temperature and stirred for 3 hours. The precipitate obtained was filtered and dried under vacuum at room temperature. The product contained 100% molar amount of p-xylene. Yield: 85%

Example 2

Preparation of Rostafuroxin Form C

A mixture of 2.50 g of rostafuroxin (amorphous or any other crystalline form) and 100 ml of diethyl ether was refluxed until the solution was clear, cooled to room temperature and stirred for 16 hours. The precipitate obtained was filtered and dried under vacuum at room temperature. The product obtained was anhydrous. Yield: 15%

Example 3

Preparation of Rostafuroxin Form C 5.00 g of rostafuroxin (amorphous or any other crystalline form) were suspended in 250 ml of toluene and warmed to reflux temperature. The solution was cooled to room temperature and, after 2 hours, the precipitate obtained was filtered and dried under vacuum at 40° C. for 40 hours. The product obtained was anhydrous. Yield: 42%

Example 4

Preparation of Rostafuroxin Form D

A mixture of 4.00 g of rostafuroxin (amorphous or any other crystalline form) and 20 ml of ethyl acetate was refluxed until the solution was clear. 30 ml of diisopropyl ether were slowly added. The solution was cooled to room temperature and stirred for 72 hours. The precipitate obtained was filtered and dried under vacuum at 35° C. for 2 hours. The product obtained was anhydrous. Yield: 82%

Example 5

Preparation of Rostafuroxin Form E

A mixture of 4.00 g of rostafuroxin (amorphous or any other crystalline form) and 30 ml of isopropanol was refluxed until the solution was clear. 15 ml of diisopropyl ether were slowly added at the same temperature. The solution was cooled to room temperature and stirred for 65 hours. The precipitate obtained was filtered, washed with diisopropyl ether and dried under vacuum at 25° C. The product contained 30% molar amount of isopropyl alcohol. Yield: 78%

Example 6

Preparation of Rostafuroxin Form F

A mixture of 5.00 grams of rostafuroxin (amorphous or any other crystalline form) and 50 ml of absolute ethanol was stirred until clearness. This solution was than added dropwise into 250 ml of water at room temperature under vigorous stirring at room temperature. At the end of addiction, the mixture was filtered and washed with deionized water. The product was dried under vacuum at 40° C. for 16 hours. The product contained 10.6% of water, corresponding to about 2.5 moles of water per mole of rostafuroxin (rostafuroxin.2.5$H_2O$). Yield: 55%. Due to the low solubility of this crystalline form in water, it has been found that the yield can be increased up to about 90% by increasing the amount of water to which the ethanol solution is added dropwise. The X-ray diffractogram of this product is reported in FIG. 6.

Comparative Example 4

Preparation of Rostafuroxin Form F

A mixture of 5.00 g of rostafuroxin (amorphous or any other crystalline form) and 30 ml of absolute ethanol was refluxed until the solution was clear. 1 ml of water was added and the solution was still refluxed until clearness, cooled to room temperature and stirred at this temperature for about 16 hours. The precipitate was filtered, washed with ethanol and dried under vacuum at 40° C. for 16 hours.

The product contained 5.34% of water. Despite the difference in water content the X-ray diffractogram obtained with this product was essentially the same as that reported in FIG. 6, i.e. the position and the relative intensity of the peaks was the same. Yield: 58%.

Comparative Example 5

Preparation of Rostafuroxin Form F

A mixture of 4.00 g of rostafuroxin (amorphous or any other crystalline form) and 20 ml of water was warmed to 50° C. This suspension was stirred at this temperature for 2 hours. After cooling to room temperature the solid was filtered and dried under vacuum at 25° C. for 16 hours. The product contained 5.11% of water. Despite the difference in water content the X-ray diffractogram obtained with this product was essentially the same as that reported in FIG. 6, i.e. the position and the relative intensity of the peaks was the same. Yield: 90%.

Comparative Example 6

Preparation of Rostafuroxin Form F

A mixture of 4.00 g of rostafuroxin (amorphous or any other crystalline form) and 1 liter of water was refluxed until the solution was clear, cooled to room temperature and stirred at this temperature for 24 hours. The precipitate obtained was filtered, washed with water and dried under vacuum at 40° C. for 16 hours. The product contained 6.44% of water. Despite the difference in water content the X-ray diffractogram obtained with this product was essentially the same as that reported in FIG. 6, i.e. the position and the relative intensity of the peaks was the same. Yield: 70%.

Comparative Example 7

Preparation of Rostafuroxin Form F 5.00 grams of rostafuroxin (amorphous or any other crystalline form) were dissolved in ethanol and the solvent was removed under reduced pressure. The solid obtained was allowed to absorb water in a saturated moist atmosphere to constant weight and contained from 9.77 to 10.97% of water. Despite the difference in water content the X-ray diffractogram obtained with this product was essentially the same as that reported in FIG. 6, i.e. the position and the relative intensity of the peaks was the same.

Comparative Example 8

Preparation of Rostafuroxin Form G 4.40 g of rostafuroxin (amorphous or any other crystalline form) were suspended in 50 ml of a mixture acetone/water 9/1 and warmed to reflux temperature until clearness. The solution was cooled to room temperature and, after 30 minutes, the precipitate obtained was filtered and dried under vacuum at 40° C. for 6 hours. The product contained 50% molar (0.5 molar amount) acetone. Yield: 64%

Example 7

Preparation of Rostafuroxin Form H

A mixture of 5.00 g of rostafuroxin (amorphous or any other crystalline form) and 150 ml of m-xylene was refluxed until the solution was clear, cooled to room temperature and stirred for 3 hours. The precipitate obtained was filtered and dried under vacuum at 40° C. for 16 hours. The product obtained was anhydrous. Yield: 72%

Comparative Example 9

Preparation of Amorphous Rostafuroxin 2 g of rostafuroxin were suspended in 50 ml of a mixture dichloromethane/ethyl acetate 8/2 and warmed to reflux temperature until clearness. The solvents were removed under reduced pressure and the solid dried under vacuum at 40° C. for 16 hours.

The X-ray diffraction spectra of the crystalline products obtained in accordance with the examples are as follows:

| Anticathode: Cu Kα Voltage: 50 kV Angle (° 2θ) | Filter: Ni Current: 30 mA Relative Intensity |
|---|---|
| FORM A | |
| 6.52 | 8.4 |
| 12.83 | 100.0 |
| 13.03 | 61.6 |
| 14.54 | 56.1 |
| 17.01 | 9.6 |
| 17.44 | 25.5 |
| 19.37 | 19.9 |
| 19.56 | 5.1 |
| 21.04 | 8.0 |
| 22.21 | 11.2 |
| 25.90 | 5.8 |
| 26.06 | 5.0 |
| 29.05 | 4.9 |
| 32.95 | 11.5 |
| FORM B | |
| 8.92 | 20.2 |
| 11.17 | 8.7 |
| 13.56 | 41.1 |
| 14.37 | 22.6 |
| 15.55 | 23.6 |
| 15.91 | 22.7 |
| 16.29 | 18.0 |
| 17.70 | 100.0 |
| 19.74 | 9.9 |
| 20.38 | 11.8 |
| 21.71 | 9.8 |
| 23.09 | 9.2 |
| 23.61 | 8.9 |
| 24.30 | 10.3 |
| 26.56 | 16.4 |
| 27.16 | 11.8 |
| 27.73 | 8.6 |
| FORM C | |
| 2.05 | 12.7 |
| 5.47 | 7.1 |
| 7.23 | 16.5 |
| 8.33 | 56.1 |
| 10.84 | 42.7 |
| 11.56 | 17.6 |
| 12.04 | 33.0 |
| 13.41 | 35.2 |
| 13.95 | 41.6 |
| 14.49 | 55.8 |
| 14.96 | 51.8 |
| 16.02 | 77.0 |
| 16.53 | 100.0 |
| 17.59 | 38.5 |
| 19.46 | 23.6 |
| 21.72 | 37.7 |
| 23.11 | 27.1 |
| 24.41 | 17.7 |
| 25.45 | 14.3 |
| 26.51 | 15.1 |
| 27.17 | 9.3 |
| 27.99 | 6.8 |
| FORM D | |
| 8.21 | 30.9 |
| 13.16 | 35.5 |
| 13.32 | 42.7 |
| 14.27 | 39.3 |
| 14.46 | 32.4 |
| 15.23 | 72.8 |
| 15.97 | 30.0 |
| 16.08 | 32.9 |
| 16.92 | 61.9 |
| 17.11 | 100.0 |
| 18.13 | 26.9 |
| 18.88 | 17.6 |
| 18.97 | 16.2 |
| 19.38 | 13.1 |
| 19.56 | 15.3 |
| 20.28 | 19.4 |

| Anticathode: Cu Kα Voltage: 50 kV Angle (° 2θ) | Filter: Ni Current: 30 mA Relative Intensity |
|---|---|
| 21.17 | 16.1 |
| 22.18 | 24.3 |
| 22.32 | 27.3 |
| 22.55 | 28.4 |
| 23.14 | 36.2 |
| 23.68 | 22.5 |
| 23.99 | 13.6 |
| 24.41 | 15.8 |
| 25.79 | 16.2 |
| 26.63 | 15.6 |
| 27.54 | 23.0 |
| 27.80 | 16.1 |
| 28.23 | 12.2 |
| 29.04 | 21.5 |
| 30.64 | 14.5 |
| 31.67 | 18.0 |
| 34.37 | 15.9 |
| 36.47 | 27.3 |
| 39.18 | 16.6 |
| 39.43 | 15.9 |
| FORM E | |
| 3.60 | 47.9 |
| 6.98 | 51.7 |
| 10.33 | 27.1 |
| 13.26 | 100.0 |
| 14.07 | 52.3 |
| 14.65 | 15.7 |
| 15.61 | 21.4 |
| 16.43 | 42.4 |
| 17.65 | 16.2 |
| 18.83 | 11.8 |
| 20.57 | 60.7 |
| 21.42 | 13.4 |
| 21.68 | 13.8 |
| 22.99 | 13.7 |
| 23.97 | 19.2 |
| 24.38 | 15.2 |
| 27.43 | 28.4 |
| 28.90 | 9.2 |
| FORM F | |
| 3.56 | 6.7 |
| 6.98 | 12.2 |
| 10.36 | 5.7 |
| 13.60 | 100.0 |
| 14.44 | 39.1 |
| 15.66 | 76.0 |
| 16.01 | 73.5 |
| 16.47 | 54.1 |
| 17.09 | 28.8 |
| 17.80 | 31.0 |
| 20.56 | 22.9 |
| 21.73 | 16.8 |
| 21.97 | 14.4 |
| 23.21 | 19.2 |
| 24.48 | 33.1 |
| 25.18 | 12.8 |
| 25.53 | 13.9 |
| 26.11 | 19.4 |
| 26.70 | 11.3 |
| 27.11 | 18.4 |
| 27.46 | 18.1 |
| 27.80 | 20.2 |
| 28.23 | 15.1 |
| 29.11 | 9.5 |
| 30.06 | 8.4 |
| 31.41 | 7.3 |
| 32.47 | 7.2 |
| 36.78 | 12.4 |
| 37.92 | 6.4 |
| 38.20 | 6.1 |
| 38.71 | 6.9 |
| FORM G | |
| 9.56 | 24.4 |
| 10.24 | 87.5 |
| 13.11 | 64.6 |
| 13.66 | 100.0 |
| 13.77 | 96.3 |
| 14.29 | 69.1 |
| 14.89 | 35.8 |
| 15.52 | 34.7 |
| 15.94 | 47.7 |
| 16.64 | 61.3 |
| 17.73 | 25.3 |
| 18.68 | 30.0 |
| 19.39 | 48.0 |
| 20.20 | 37.2 |
| 20.85 | 34.1 |
| 21.17 | 34.4 |
| 21.82 | 27.5 |
| 22.61 | 35.5 |
| 24.46 | 25.8 |
| 25.41 | 19.9 |
| 26.73 | 23.5 |
| 27.59 | 18.9 |
| 28.67 | 14.0 |
| 29.61 | 9.7 |
| FORM H | |
| 6.88 | 10.5 |
| 10.29 | 5.3 |
| 13.50 | 100.0 |
| 14.34 | 42.8 |
| 15.54 | 58.3 |
| 15.97 | 61.2 |
| 16.34 | 55.0 |
| 16.96 | 32.8 |
| 17.73 | 27.5 |
| 20.47 | 31.4 |
| 21.68 | 27.0 |
| 23.08 | 28.8 |
| 24.43 | 31.4 |
| 25.97 | 22.6 |
| 27.13 | 25.2 |
| 27.72 | 21.1 |
| 28.21 | 14.6 |
| 29.00 | 11.3 |
| 29.99 | 7.6 |
| 36.64 | 8.4 |

The invention claimed is:

1. A method for preparing crystalline, rostafuroxin Form F, consisting of dissolving rostafuroxin, amorphous, in ethanol to form a solution and then adding dropwise said solution to an excess of water at room temperature, and thereafter isolating crystalline rostafuroxin Form F having 2.5 moles of water per mole of rostafuroxin.

2. The method of claim 1, wherein the amount of water used during crystallization is in excess of the amount of ethanol.

3. A method for preparing crystalline rostafuroxin Form F, consisting of:
dissolving amorphous or crystalline rostafuroxin, in ethanol to form a solution, adding said solution dropwise to an excess of water at room temperature to form a precipitate, filtering and isolating the precipitate, washing the isolated precipitate with water and drying it under vacuum to form crystalline rostafuroxin Form F having 2.5 moles of water per mole of rostafuroxin.

4. A method for preparing crystalline rostafuroxin Form F, consisting of
dissolving amorphous or crystalline rostafuroxin in ethanol to form a solution, adding said solution dropwise to an excess of water at room temperature, and thereafter isolating ciystalline rostafuroxin Form F having 2.5 moles of water per mole of rostafuroxin.

Figure 1:
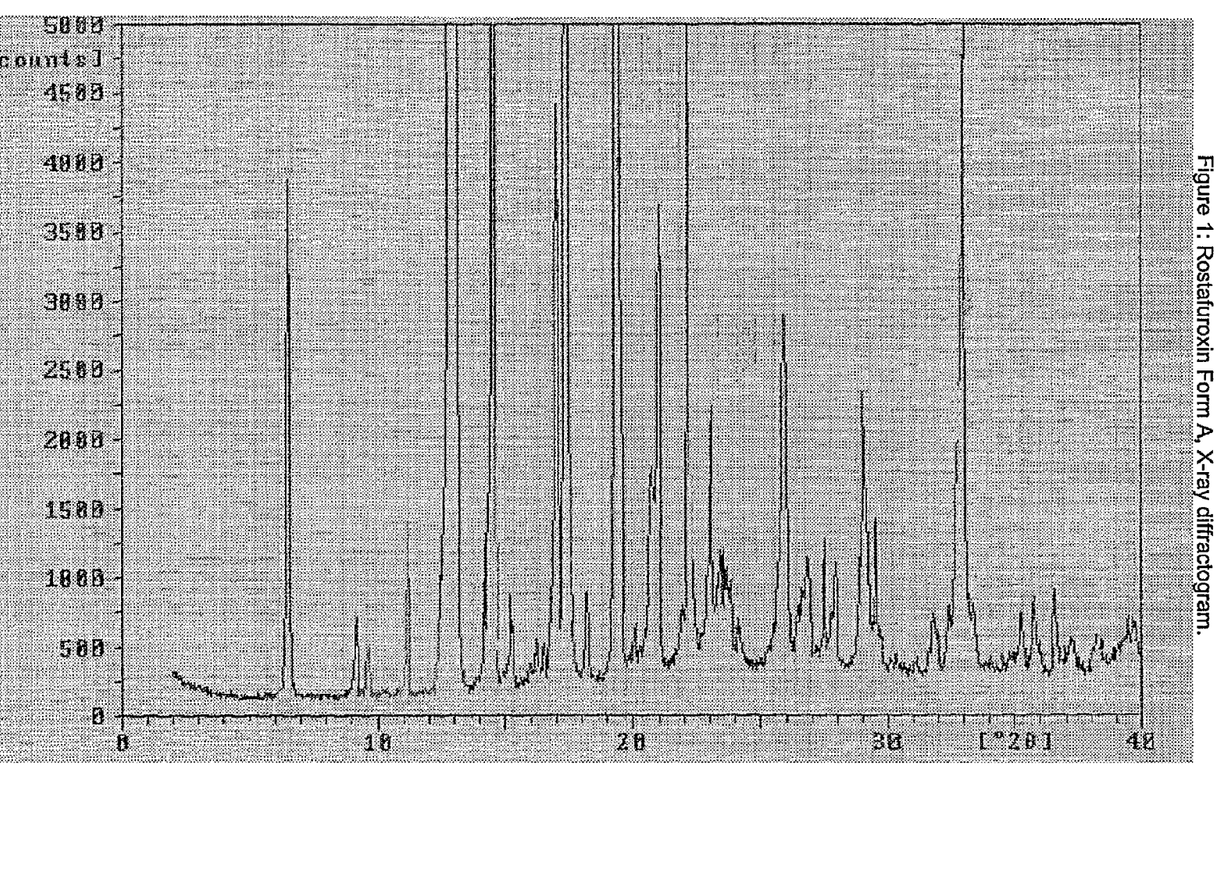
FIG. 1 shows the powder X-ray diffraction spectrum of rostafuroxin Form A.
Figure 2:
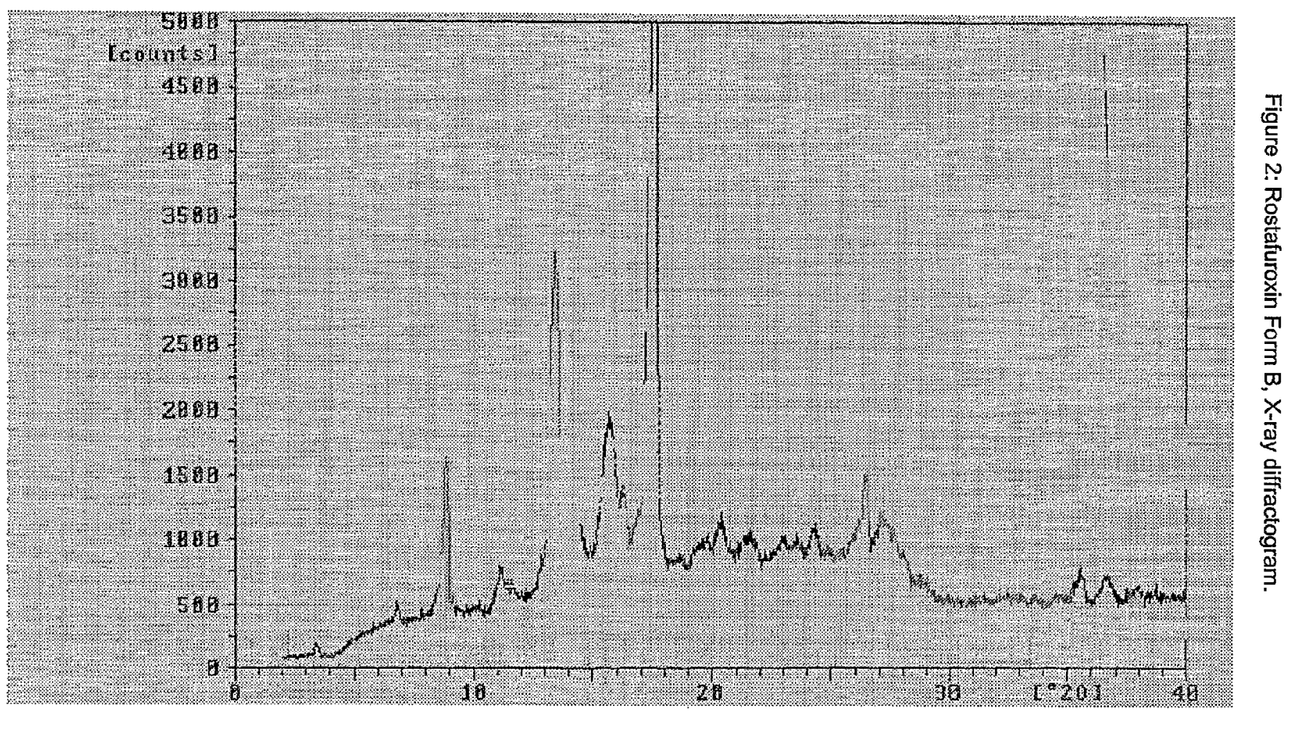
FIG. 2 shows the powder X-ray diffraction spectrum of rostafuroxin Form B.
Figure 3:
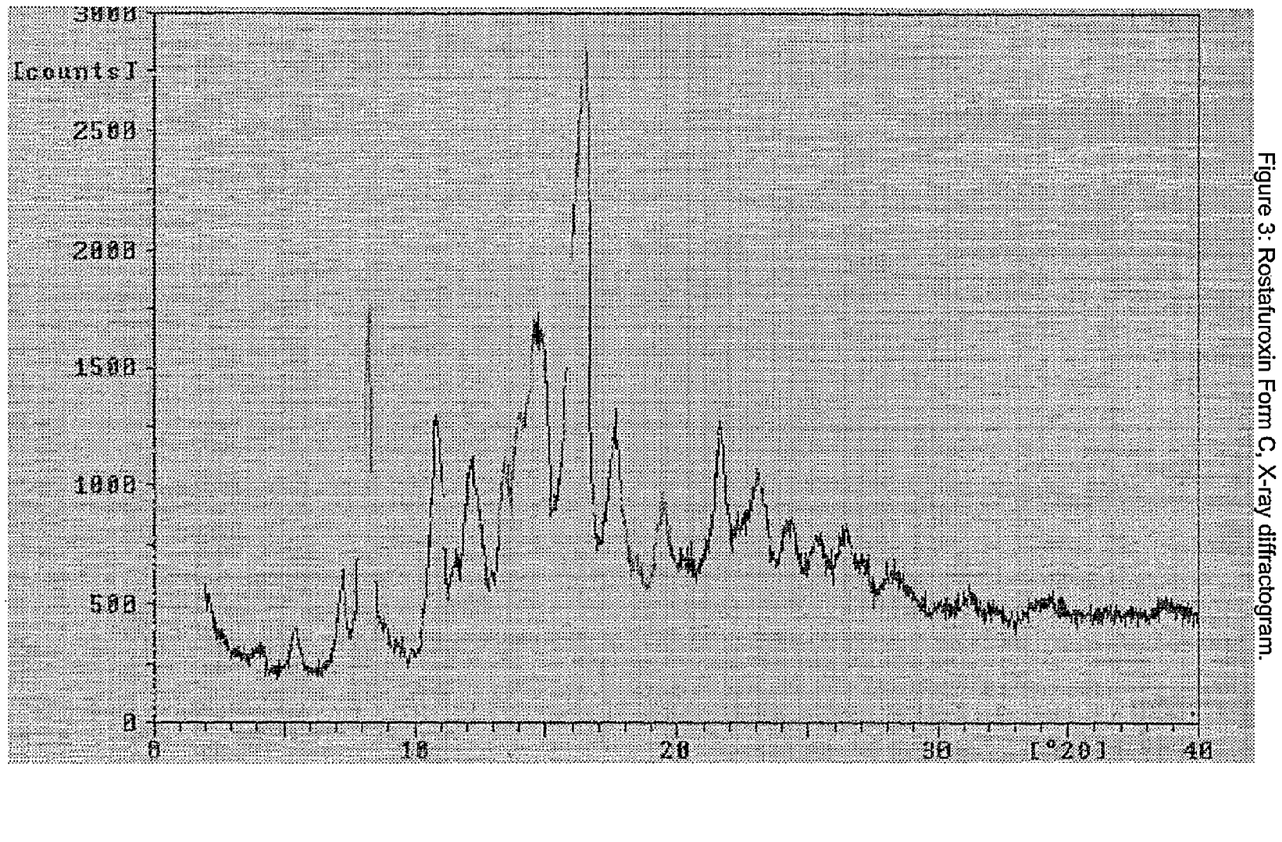
FIG. 3 shows the powder X-ray diffraction spectrum of rostafuroxin Form C.
Figure 4:
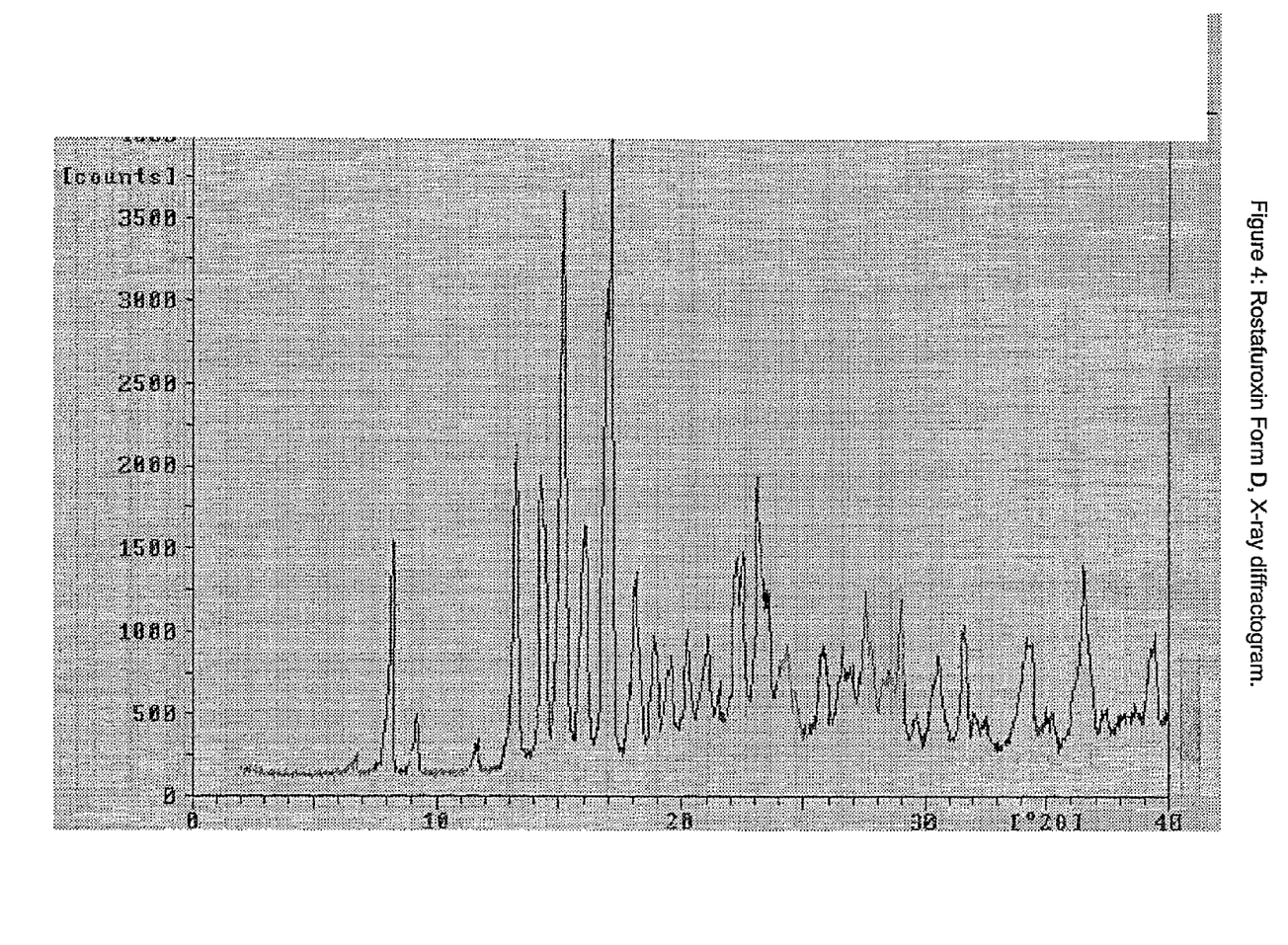
FIG. 4 shows the powder X-ray diffraction spectrum of rostafuroxin Form D.
Figure 5:
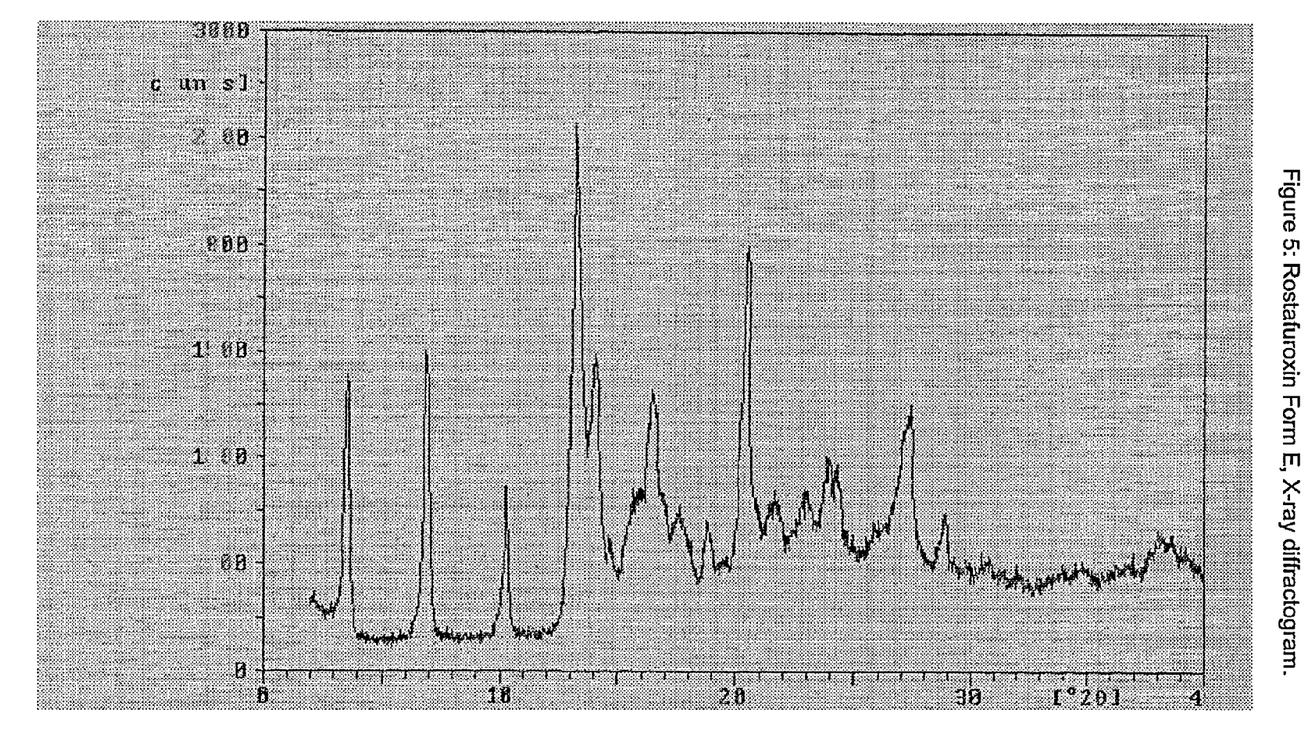
FIG. 5 shows the powder X-ray diffraction spectrum of rostafuroxin Form E.
Figure 6:
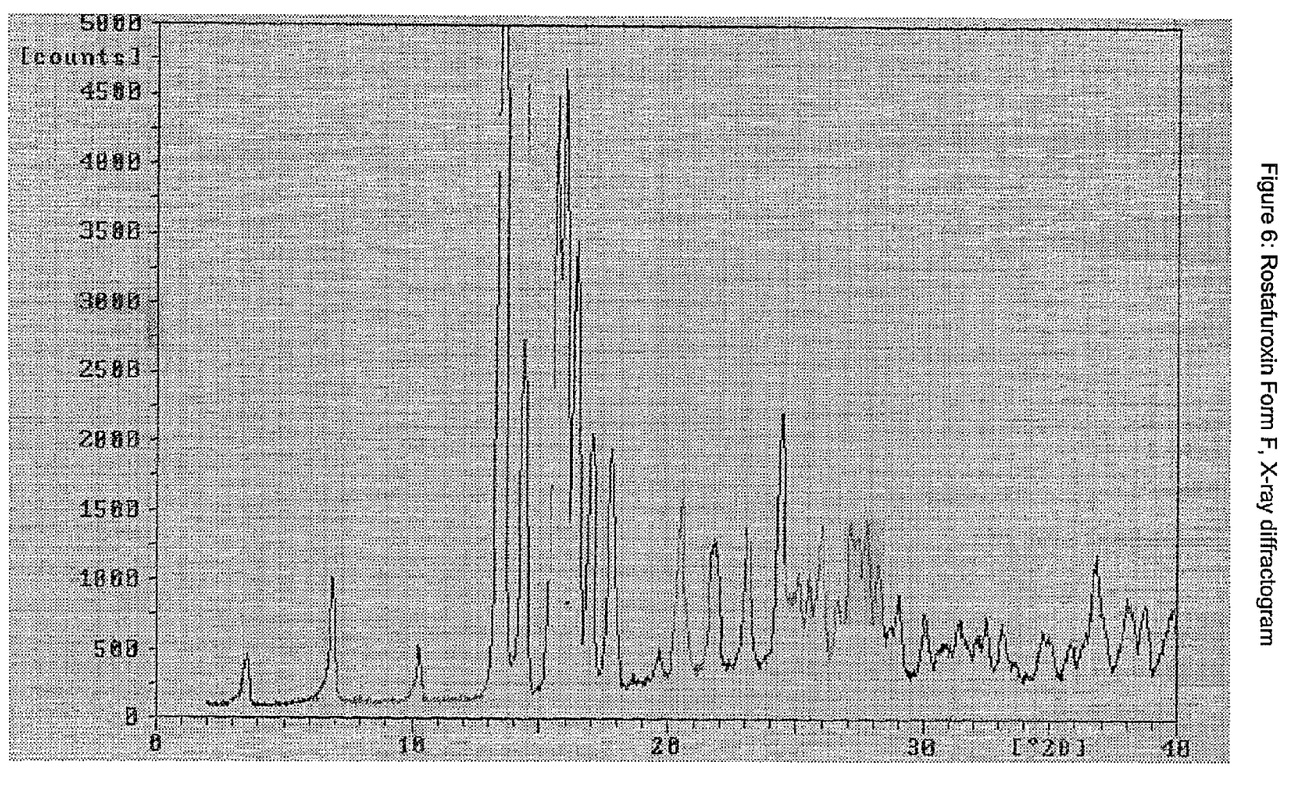
FIG. 6 shows the powder X-ray diffraction spectrum of rostafuroxin Form F.
Figure 7:
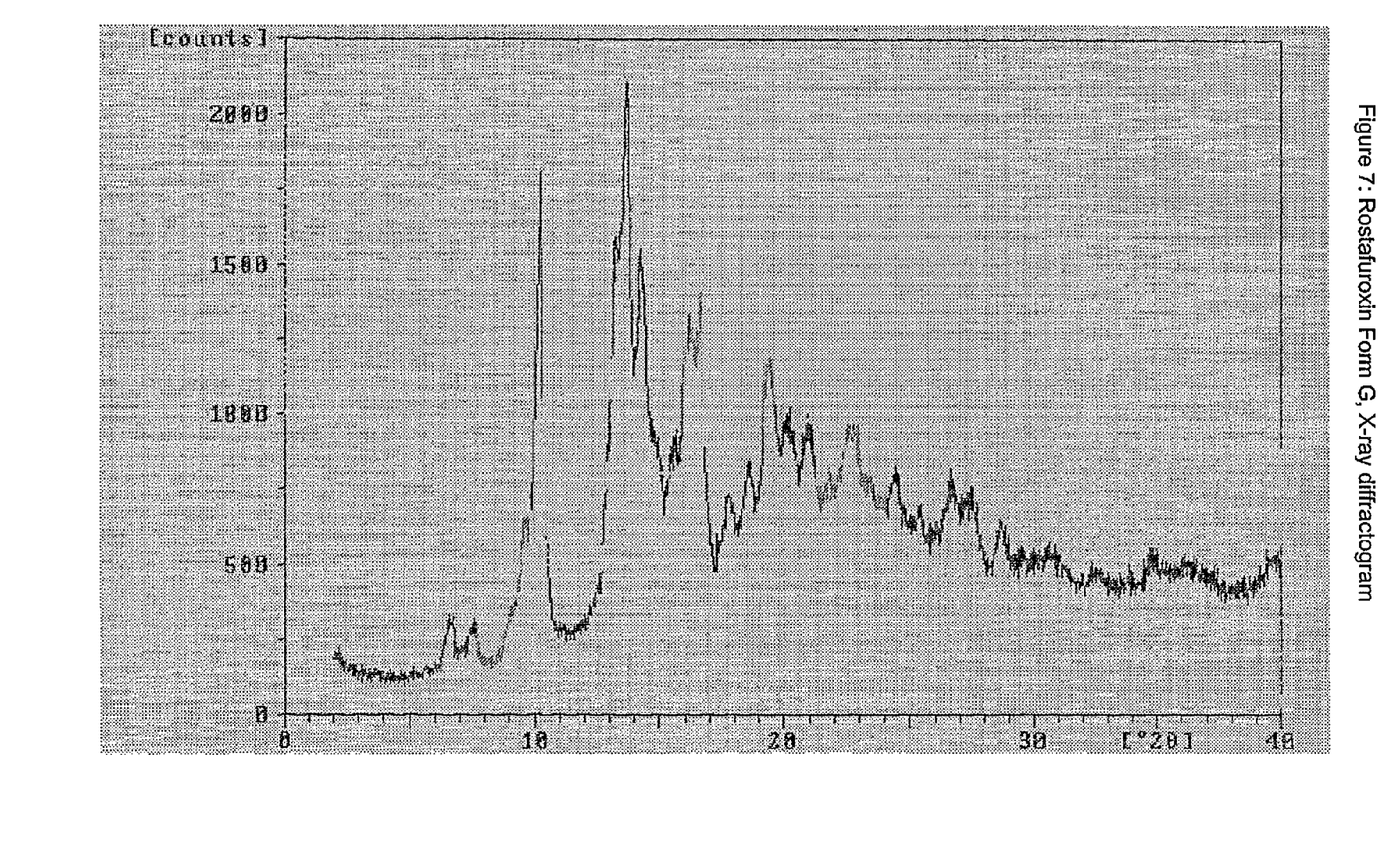
FIG. 7 shows the powder X-ray diffraction spectrum of rostafuroxin Form G.
Figure 8:
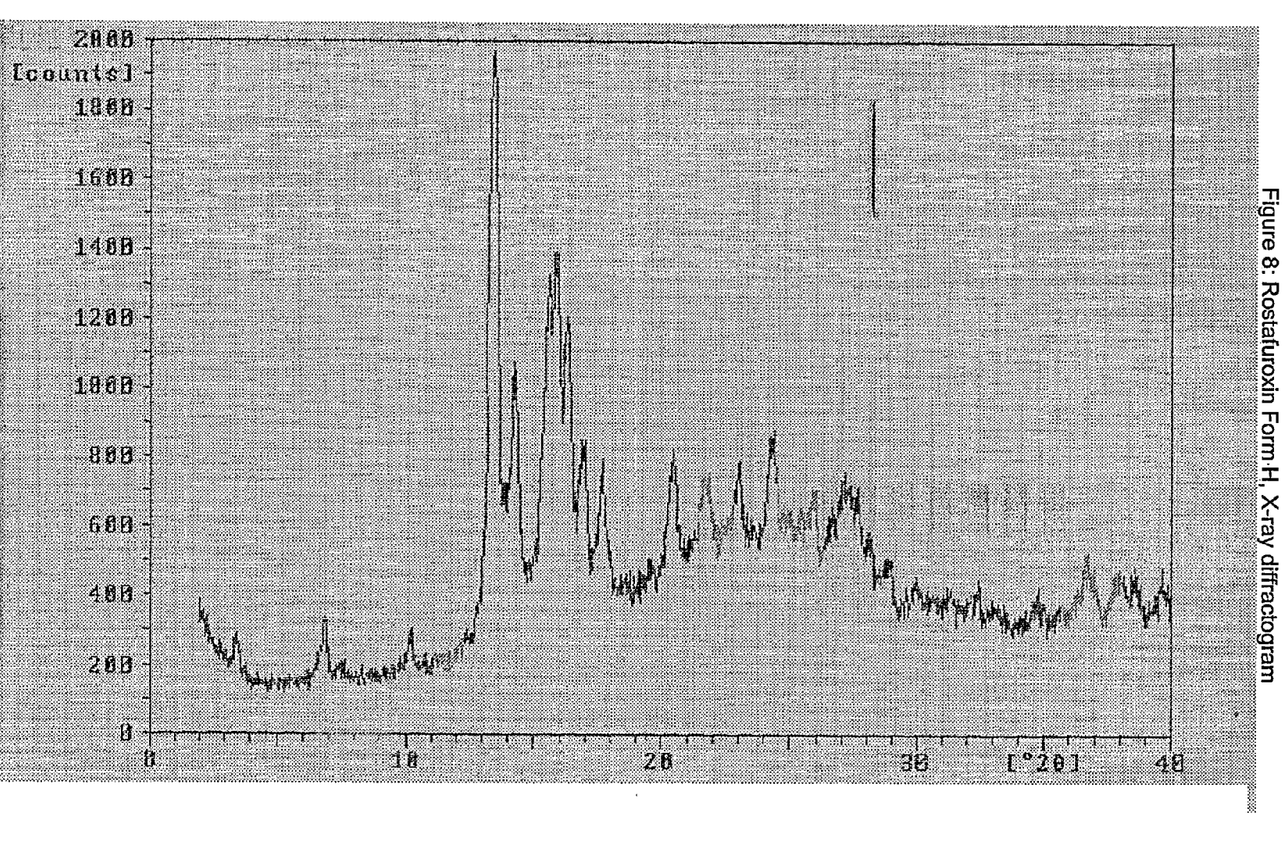
FIG. 8 shows the powder X-ray diffraction spectrum of rostafuroxin Form H.
Figure 9:
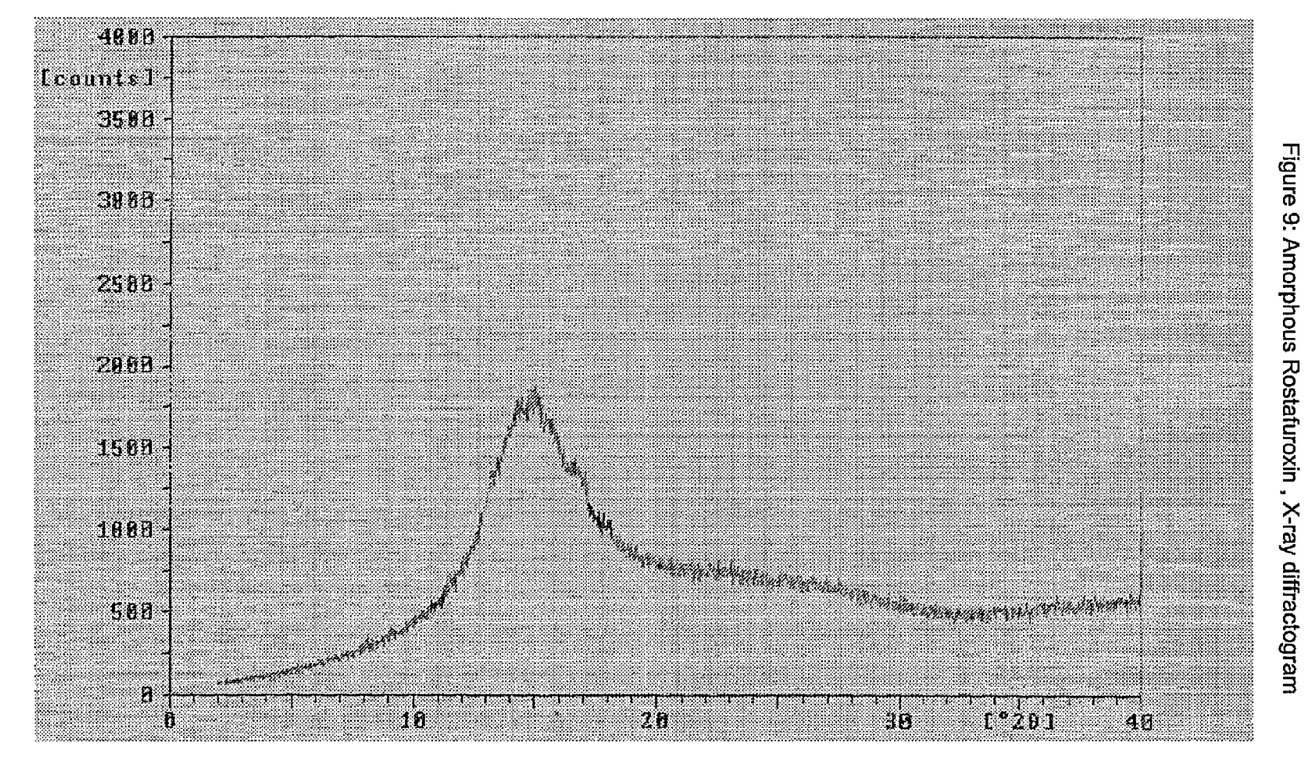
FIG. 9 shows the powder X-ray diffraction spectrum of amorphous rostafuroxin.

5. The method. of claim 1, wherein the crystalline rostafuroxin Form F having 2.5 moles of water per mole of rostafuroxin has an X-ray diffraction spectrum as shown in FIG. 6.

6. The method of claim 3, wherein the crystalline rostafuroxin Form F having 2.5 moles of water per mole of rostafuroxin has an X-ray diffraction spectrum as shown in FIG. 6.

7. The method of claim 4, wherein the crystalline rostafuroxin Form F having 2.5 moles of water per mole of rostafuroxin has an X-ray diffraction. spectrum as shown in FIG. 6.

* * * * *